United States Patent
Xie et al.

(10) Patent No.: US 9,931,097 B2
(45) Date of Patent: Apr. 3, 2018

(54) IMAGING SUBJECT MOULD MANUFACTURING METHOD, AND INDIVIDUALIZED IMAGING METHOD

(71) Applicants: RAYCAN TECHNOLOGY CO., LTD. (SU ZHOU), Suzhou, Jiangsu (CN); X-Z LAB, INC., San Ramon, CA (US)

(72) Inventors: Zizhuo Xie, San Ramon, CA (US); Qingguo Xie, Suzhou (CN)

(73) Assignees: RAYCAN TECHNOLOGY CO., LTD. (SU ZHOU), Suzhou, Jiangsu (CN); X-Z LAB, INC., San Ramon, CA (US)

( * ) Notice: Subject to any disclaimer, the term of this patent is extended or adjusted under 35 U.S.C. 154(b) by 0 days.

(21) Appl. No.: 15/307,573

(22) PCT Filed: Nov. 18, 2014

(86) PCT No.: PCT/CN2014/091421
§ 371 (c)(1),
(2) Date: Oct. 28, 2016

(87) PCT Pub. No.: WO2015/165252
PCT Pub. Date: Nov. 5, 2015

(65) Prior Publication Data
US 2017/0042499 A1   Feb. 16, 2017

(30) Foreign Application Priority Data

Apr. 30, 2014   (CN) .......................... 2014 1 0181983

(51) Int. Cl.
*A61B 6/00*   (2006.01)
*A61B 8/00*   (2006.01)
(Continued)

(52) U.S. Cl.
CPC .............. *A61B 6/582* (2013.01); *A61B 5/055* (2013.01); *A61B 6/00* (2013.01); *A61B 6/032* (2013.01); *A61B 6/037* (2013.01); *A61B 8/00* (2013.01)

(58) Field of Classification Search
CPC ......... A61B 5/055; A61B 6/00; A61B 6/0325; A61B 6/037; A61B 6/582; A61B 8/00
See application file for complete search history.

(56) References Cited

U.S. PATENT DOCUMENTS 7,157,696 B2   1/2007   White et al.
2003/0112921 A1   6/2003   Lang et al.
(Continued)

FOREIGN PATENT DOCUMENTS

CA   2512103 A1   1/2004
CN   1682236 A   10/2005
(Continued)

OTHER PUBLICATIONS

International Search Report corresponding to Application No. PCT/CN2014/091421; dated Feb. 17, 2015, with English translation.
(Continued)

*Primary Examiner* — Edward Park
(74) *Attorney, Agent, or Firm* — Cantor Colburn LLP

(57) ABSTRACT

An individualized imaging method, comprising the following steps: scanning an imaging subject mold; conducting calibration, rectification and optimization on the imaging system according to the information obtained after mold imaging: scanning the imaging subject with the calibrated, rectified and optimized imaging system; optimizing information obtained by scanning the imaging subject and the mold thereof to obtain higher quality imaging results and
(Continued)

data analysis result; and applying the higher quality imaging results and data analysis results to optimize the mold for use in the next imaging.

5 Claims, 13 Drawing Sheets

(51) Int. Cl.
*A61B 5/055* (2006.01)
*A61B 6/03* (2006.01)

(56) References Cited

U.S. PATENT DOCUMENTS

| | | | |
|---|---|---|---|
| 2010/0202001 | A1 | 8/2010 | Miller et al. |
| 2010/0290680 | A1* | 11/2010 | Declerck ............... A61B 6/037 382/128 |
| 2012/0148131 | A1 | 6/2012 | Couch et al. |
| 2017/0048400 | A1* | 2/2017 | Berfanger ............ H04N 1/6052 |

FOREIGN PATENT DOCUMENTS

| | | |
|---|---|---|
| CN | 103442644 A | 12/2013 |
| JP | 2006517433 A | 7/2006 |
| JP | 2013544605 A | 12/2013 |
| WO | 2012040611 A1 | 3/2012 |

OTHER PUBLICATIONS

1st Office Action for corresponding JP Application No. 2016-565189; dated Oct. 2, 2017.

\* cited by examiner

IMAGING SUBJECT MOULD MANUFACTURING METHOD, AND INDIVIDUALIZED IMAGING METHOD

This application is a national phase of International Application No. PCT/CN2014/091421, titled "IMAGING SUBJECT MOULD MANUFACTURING METHOD, AND INDIVIDUALIZED IMAGING METHOD", filed on Nov. 18, 2014, which claims priority to Chinese Patent Application No. 201410181983.3, filed with the State Intellectual Property Office of People's Republic of China on Apr. 30, 2014 and titled "IMAGING SUBJECT MOULD MANUFACTURING METHOD, AND INDIVIDUALIZED IMAGING METHOD", which are incorporated herein by reference in their entirety.

FIELD

The present disclosure relates to the field of medical imaging technology, and more particularly to a method for manufacturing a mould of an object to be imaged and an individualized imaging method.

BACKGROUND

As shown in FIGS. 1-4, in the conventional medical imaging technology, the priori knowledge of an object to be imaged is not fully utilized in order to obtain higher diagnosis accuracy, less radiation injury and lower cost. Such as, a cylinder used as a prosthesis is imaged to obtain image data information Img0 when PET imaging is performed. The image data information Img0 is utilized for system calibration and system correction. Then a body is imaged by the calibrated and corrected imaging system to obtain image data information Img1. This process which uses a cylinder as a prosthesis to calibrate and correct the imaging system is rough. The image system itself is not optimized.

Besides, for some combined imaging systems, such as a PET-CT combined imaging system, patients may experience CT before experiencing PET-CT. But, when the PET-CT is performed, they have to experience CT imaging in the PET-CT once again to correct the attenuation. Generally speaking, the CT in the PET-CT has low performance and great radiation. In the diagnoses of some diseases, such as physical examination, the result of the CT is not needed, which adds the amount of radiation to the patients and is harmful to health of the patients.

Thus, it is necessary to provide a new individualized imaging method to overcome the problems existed in the conventional technology. This method fully utilizes the priori knowledge of human. By establishing a mould for an individual, using the mould to calibrate, correct and optimize the system and utilizing the information of the mould to optimize the imaging result, imaging result and data analysis result with a higher quality may be achieved.

SUMMARY

In view of the above, the object of the disclosure is to provide a method for manufacturing a mould of an object to be imaged and an individualized imaging method which improves the imaging quality. The core of this imaging method is that it may utilize the priori knowledge of human to establish a mould. Image data information of the mould may be utilized to optimize the imaging system and the image data information of the object to be imaged. And further more, the mould may be optimized. By repeating this, an imaging result and data analysis result with a higher quality may be obtained.

In order to achieve above objects, technical solutions of the disclosure are provided as follows.

A method for manufacturing a mould of an object to be imaged is provided. The mould is manufactured according to density information or function information obtained by imaging the object to be imaged.

A method for manufacturing a mould of an object to be imaged is provided. The mould is made with information obtained as follows. The objects to be imaged are classified. Then for each class, a database generated by imaging the objects to be imaged through various imaging systems is processed such as averaged.

An individualized imaging method is provided, which includes:

S1, obtaining image data information Img0 of a mould of an object to be imaged;

S2, calibrating, correcting and optimizing an imaging system with the image data information Img0, scanning and imaging, by the calibrated, corrected and optimized imaging system, the object to be imaged, to obtain an image data information Img1; and S3, optimizing the image data information Img0 and the image data information Img1 to obtain an imaging result and data analysis result Img10 with a higher quality.

An individualized imaging method is provided, which includes:

S1, obtaining image data information Img0 of a mould of an object to be imaged;

S2, imaging the object to be imaged, to obtain image data information Img1, and optimizing the image data information Img0 and the image data information Img1 to obtain an imaging result and data analysis result Img10 with a higher quality; and S3, optimizing the mould via the imaging result and data analysis result Img10 with the higher quality obtained in S2.

An individualized imaging method is provided, which includes:

S1, imaging, by an imaging system A, a mould of an object to be imaged, to obtain image data information Img0;

S2, calibrating, correcting and optimizing an imaging system B with the image data information Img0, scanning and imaging, by the calibrated, corrected and optimized imaging system B, the object to be imaged, to obtain an image data information Img1; and S3, processing the image data information Img0 and the image data information Img1 to obtain an A-B fused imaging result and data analysis result Img10.

An individualized imaging method is provided, which includes:

S1, imaging, by an imaging system A of an A-B combined imaging system, a mould of an object to be imaged, to obtain image data information Img0;

S2, calibrating, correcting and optimizing an imaging system B of the A-B combined imaging system with the image data information Img0, performing, by the A-B combined imaging system with the calibrated, corrected and optimized imaging system B, combined imaging on the object to be imaged, to obtain an image data information Img1; and S3, processing the image data information Img0 and the image data information Img1 to obtain an A-B fused imaging result and data analysis result Img10.

An individualized imaging method is provided, which includes:
- S1, imaging, by an imaging system A of an A-B combined imaging system, a mould of an object to be imaged, to obtain image data information Img0;
- S2, imaging, by the imaging system A of the A-B combined imaging system, the object to be imaged, to obtain image data information Img1;
- S3, processing the image data information Img0 and the image data information Img1 to obtain an integrated image data information Img2, and calibrating, correcting and optimizing an imaging system B of the A-B combined imaging system with the image data information Img2;
- S4, imaging, by the calibrated, corrected and optimized imaging system B, the object to be imaged to obtain image data information Img3; or performing, by the A-B combined imaging system with the calibrated, corrected and optimized imaging system B, combined imaging on the object to be imaged to obtain the image data information Img3; and
- S5, processing the image data information Img1 and Img3 or processing the image data information Img0 and Img3 or processing the image data information Img0, Img1 and Img3 or processing the image data information Img2 and Img3, to obtain an A-B fused imaging result and data analysis result Img10.

From the above technical solutions, the individualized imaging methods of the embodiments of the disclosure fully utilize the priori knowledge of human. A mould is established for an individual. The image data information of the mould may be utilized to optimize the imaging system and/or the image data information of the object to be imaged, and the mould may be optimized further. By repeating this, the imaging result and data analysis result with the higher quality may be obtained.

Comparing with the conventional technology, the advantages of the disclosure includes:
(1) the image data information of the object to be imaged is further optimized by the imaging result of the mould, further more the imaging result and data analysis result with the higher quality may be obtained;
(2) the imaging system is corrected and optimized by the imaging result of the mould, thereby it makes the imaging system in the state most suitable for the object to be imaged, further more the imaging result and data analysis result with the higher quality may be obtained;
(3) the imaging result and data analysis result with the higher quality may be obtained by using the mould, then the mould is optimized with the imaging result and data analysis result with the higher quality; by repeating this, the image data information obtained after imaging the mould is more accurate;
(4) for imaging systems with greater radiation, the amount of radiation suffered by the object to be tested may be reduced by imaging the mould, rather than imaging the actual object to be tested.

BRIEF DESCRIPTION OF THE DRAWINGS

In order to describe technical solutions in embodiments of the present application or the conventional technology more clearly, hereinafter drawings to be used in the description of the embodiments or the conventional technology are introduced simply. Apparently, the drawings described below only describe some embodiments of the present application. Those skilled in the art may obtain other drawings based on these drawings without any creative work.

DETAILED DESCRIPTION OF EMBODIMENTS

In order to make those skilled in the art understand the technical solutions of the embodiments of the disclosure more clearly, hereinafter embodiments of the disclosure are further described specifically in conjunction with drawings and implementation modes.

Figure 1:
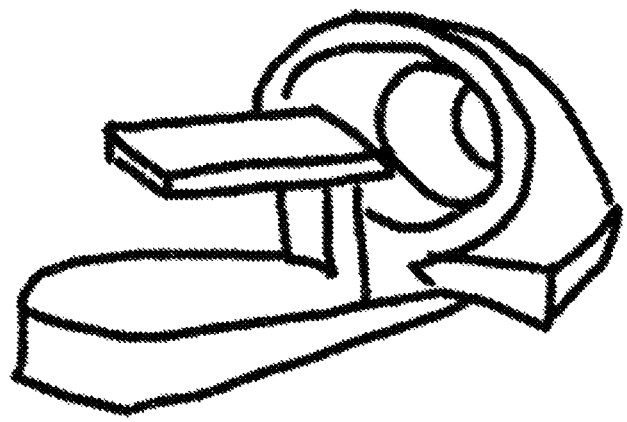
FIG. 1 is a schematic diagram of an imaging system in the conventional technology.
Figure 2:
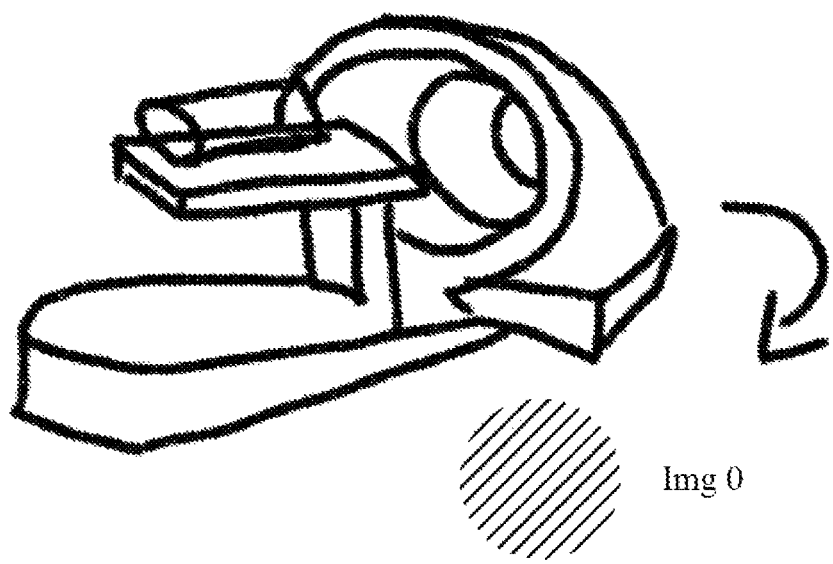
FIG. 2 is a schematic diagram illustrating imaging a cylinder as a prosthesis by using the imaging system in FIG. 1.
Figure 3:
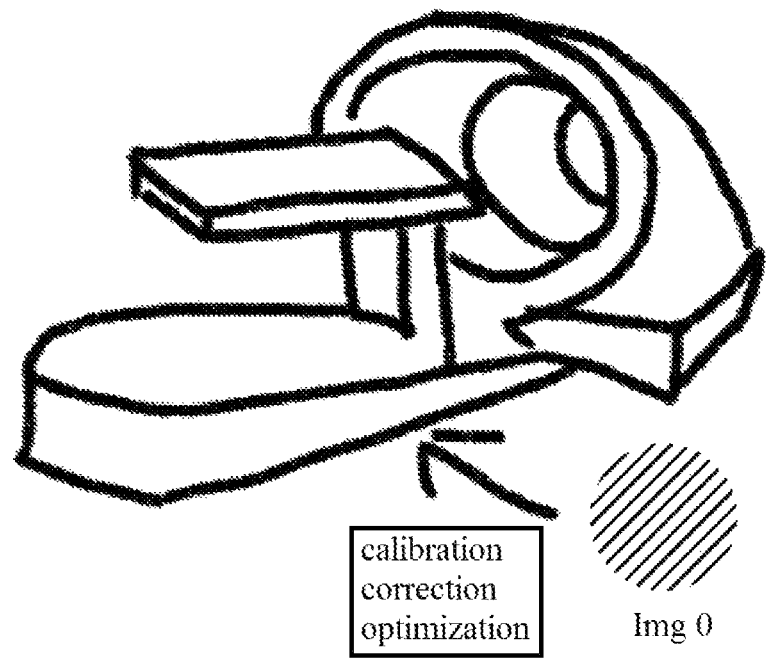
FIG. 3 is a schematic diagram illustrating calibrating, correcting and optimizing the imaging system with image data information of the cylinder obtained by the imaging system in FIG. 2.
Figure 4:
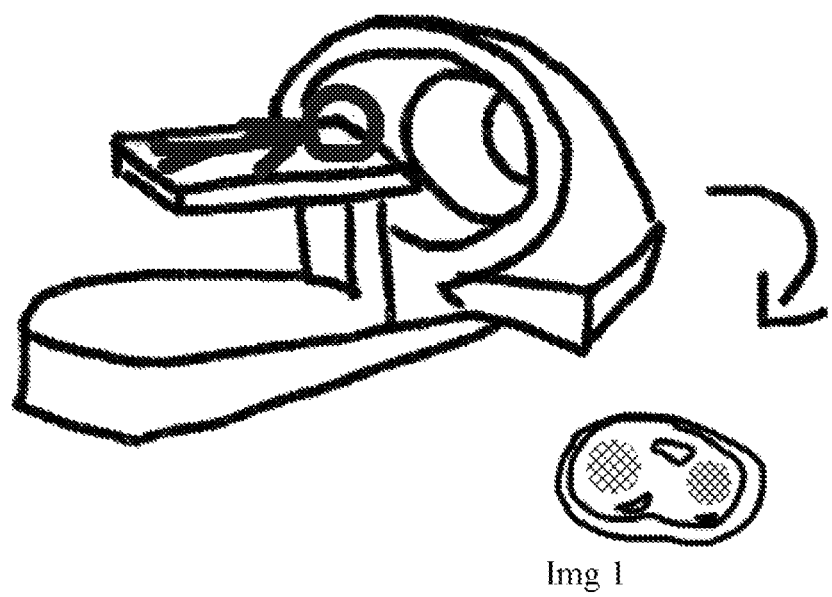
FIG. 4 is a schematic diagram illustrating imaging a body by using the calibrated, corrected and optimized imaging system in FIG. 3.
Figure 5:
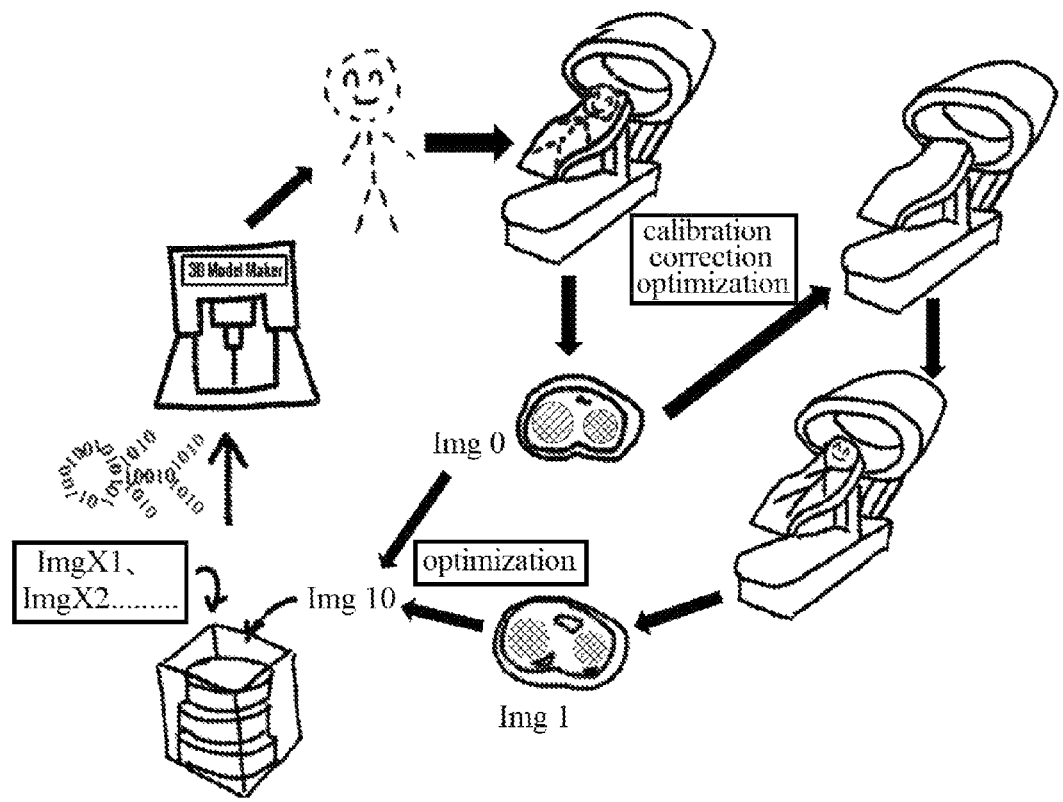
FIG. 5 illustrating a concept of an individualized imaging method of the disclosure.

As shown in FIG. 5, an individualized imaging method is provided by the disclosure. According to the imaging method, a mould of an object to be imaged made by a 3D mould manufacturing device is scanned. An imaging system is calibrated, corrected and optimized by information Img0 obtained by scanning the mould. Imaging information Img1 is obtained by using the calibrated, corrected and optimized imaging system to scan the imaging object. Imaging results and data analysis results Img10 with a higher quality are obtained by optimizing the information Img0 and Img1 obtained by scanning the object to be imaged and the mould. Some imaging results and data analysis results Img10 with a higher quality are stored in a database. Of course, the database may also include imaging results of various imaging systems which multiple objects to be imaged have experienced. A new mould is made according to the database, which may be used circularly in the next imaging of the object to be imaged or other occasions in which the mould is needed. The method of obtaining a mould by processing multiple imaging results of multiple objects to be imaged is as follows: classifying the objects to be imaged; processing, such as averaging, the database generated by imaging the objects to be imaged of the class by various imaging systems; making the mould with the obtained information from database processing.

The individualized imaging method of the embodiments of the disclosure fully utilizes the priori knowledge of human. Moulds are established one by one for individuals. The image data information of the mould may be utilized to optimize the imaging system and the image data information of the object to be imaged, and the mould may be optimized further. By repeating this, the imaging result and data analysis result with the higher quality may be obtained.

A variety of new imaging methods may be realized subsequently by using the concept of the mould.

The mould of the object to be imaged of the disclosure may be made according to density information or function information obtained by an imaging system imaging the object to be imaged. Such as, the mould may be the density information or the function information obtained by the imaging system of CT, MRI, PET, DR, CR and so on. The density information may be generally called structure information. That is, the material with the same density as human tissues is utilized to simulate different organs or tissues. The function information is simulated by reserving corresponding space in the mould to add drug taking part in relative function activities.

According to the disclosure, instead of information of a single individual, the mould of an object to be imaged may be established with information obtained as follows: classifying the objects to be imaged, processing, such as averaging, the database generated by imaging the objects to be imaged of the class through various imaging systems. This method lies in that people may experience imaging several times in real life. The imaging of those people may be classified. For each class, people may be imaged by various imaging systems. An average value is obtained by processing, such as averaging, the imaging database of the class. Then a mould is established with the average value. The classification standard is not limited specifically. The classification criterion may be an organ or may be imaging similarity.

The moulds established by the above two methods has a size equal to or in proportion to the objects to be imaged. Of course, on some special occasions or for some special requirements, the size of the moulds may not be equal to or in proportion to the objects to be imaged.

The mould may be made to be equal in size or in proportion by hand or by 3D module manufacturing devices and methods, such as 3D printing or injection molding or die casting and so on.

There are multiple embodiments of the individualized imaging methods of the disclosure. Hereinafter the technical solutions of the embodiments of the disclosure are described specifically.

Embodiment 1

As shown in FIG. 7 to FIG. 10, an individualized imaging method of the disclosure includes the following steps:
S1, obtaining image data information Img0 of a mould of an object to be imaged;
S2, calibrating, correcting and optimizing an imaging system with the image data information Img0, scanning and imaging, by the calibrated, corrected and optimized imaging system, the object to be imaged to obtain image data information Img1; and S3, optimizing the image data information Img0 and the image data information Img1 to obtain an imaging result and data analysis result Img10 with a higher quality.

Figure 6:
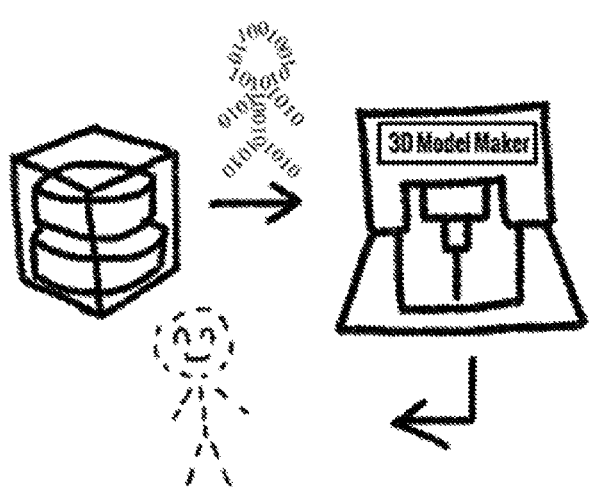
FIG. 6 is a flow chat illustrating manufacturing a mould with a 3D module manufacturing device in an individualized imaging method of the disclosure.
Figure 7:
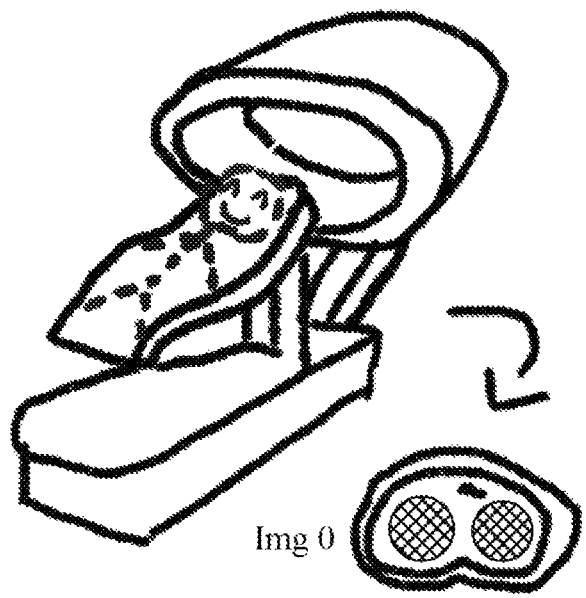
FIG. 7 is a schematic diagram illustrating imaging the mould manufactured in FIG. 6 by using an imaging system in an individualized imaging method of the disclosure.
Figure 8:
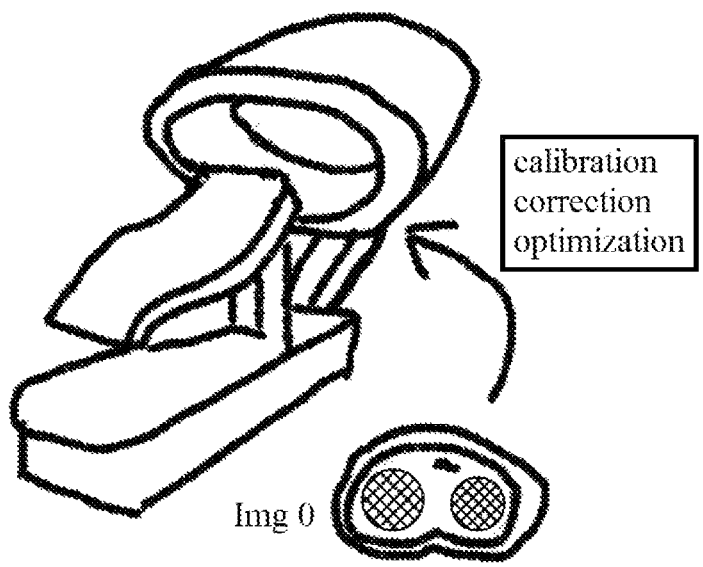
FIG. 8 is a schematic diagram illustrating calibrating, correcting and optimizing the imaging system with image data information of the mould obtained in FIG. 7 in an individualized imaging method of the disclosure.
Figure 9:
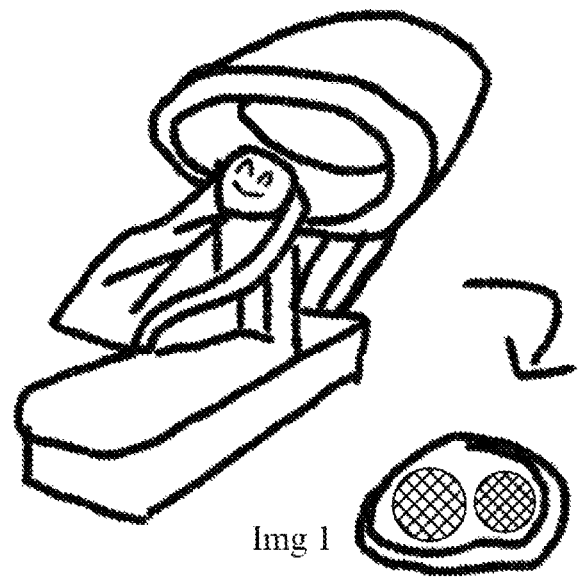
FIG. 9 is a schematic diagram illustrating imaging a body by using the calibrated, corrected and optimized imaging system in FIG. 8 in an individualized imaging method of the disclosure.
Figure 10:
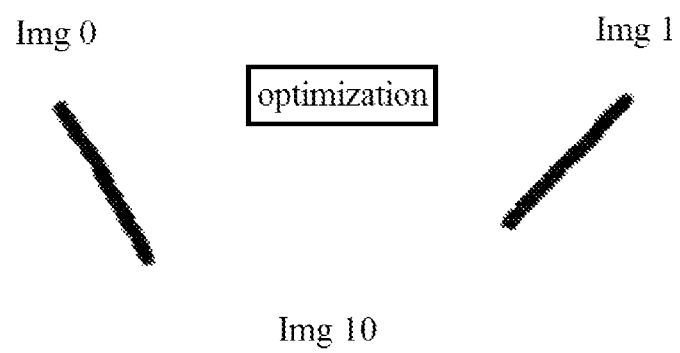
FIG. 10 illustrating obtaining a new image result and data analysis result by optimizing the image data information of the mould obtained in FIG. 7 and the image data information of the body obtained in FIG. 9 in an individualized imaging method of the disclosure.

As shown in FIG. 6, a mould is made by hand or by a 3D module manufacturing device and method, such as 3D printing or injection molding or die casting and so on, before the step S1 of the embodiment.

The image data information Img0 in the step S1 is obtained by obtaining data of the mould and extracting parameters from the data. Alternatively, the image data information Img0 in the step S1 is obtained directly from the imaging operation of the imaging system.

Figure 11:
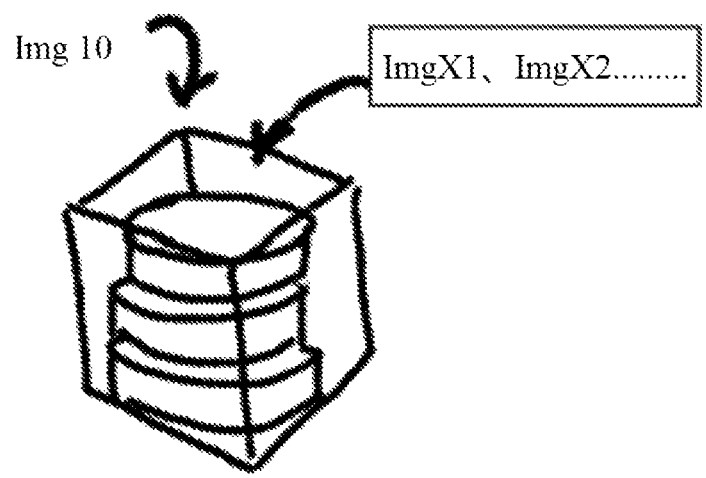
FIG. 11 illustrating a concept of obtaining a plurality of human images by imaging in which the plurality of human images may be classified in an individualized imaging method of the disclosure.

As shown in FIG. 11, FIG. 11 indicates a material library. The material library includes imaging results and data analysis results Img10 of objects to be imaged. A database is established for Img10. According to one of the mould manufacturing methods, for every single object to be imaged, the imaging results and data analysis results in the past are processed to make the mould. According to another method, image results and data analysis results Img10 of several people are classified into ImgX1, ImgX2 . . . . Thus, the objects to be imaged are classified. For each class, processing, such as averaging, the database generated by imaging the objects to be imaged through various imaging systems is performed, and then the mould is made with the obtained information.

According to the embodiment, the imaging system is calibrated, corrected and optimized based on the image data information Img0 of the mould to be in a state most suitable for imaging the object to be imaged. Then the object to be imaged is imaged. At the end of the step S3, the calibrated, corrected and optimized imaging system is used to image the object to be imaged so as to obtain image data information Img1 with a relatively high quality. In order to further optimize the image data information, the image data information Img0 and the image data information Img1 may be optimized to obtain the imaging result and data analysis result with the higher quality.

The individualized imaging method of the embodiment may further include step S4: optimizing the mould with the imaging result and data analysis result with the higher quality. By repeating S1-S4, the mould is optimized gradually at the same time as obtaining the imaging results and data analysis results with the higher quality. In the future when the information of the mould is accurate enough, the object to be imaged may be completely replaced with the mould to save cost. Besides, on the other hand, when the information of the mould is accurate enough in the future, even if the object to be imaged needs imaging, it only needs an imaging system with a low radiation dose or a low cost to image the object to be imaged or it only needs to image the object to be imaged in a short time in order to achieve the advantages of saving time and cost.

Embodiment 2

An individualized imaging method of the disclosure includes the following steps:
S1, obtaining image data information Img0 of a mould of an object to be imaged;
S2, imaging the object to be imaged to obtain image data information Img1, and optimizing the image data information Img0 and the image data information Img1 to obtain an imaging result and data analysis result Img10 with a higher quality; and
S3, optimizing the mould via the imaging result and data analysis result Img10 with the higher quality obtained in S2.

In the embodiment, the image data information Img0 in the step S1 is obtained by obtaining data of the mould and extracting parameters from the data. Alternatively, the image data information Img0 in the step S1 is obtained directly from imaging operation of the imaging system.

The difference between the present embodiment and the embodiment 1 is that the imaging system is not calibrated, corrected and optimized with the image data information Img0. The present embodiment is suitable for some occasions in which it can not or there is no need to optimize the imaging system. The imaging result and data analysis result Img10 with the higher quality is obtained directly by optimizing the image data information Img1 with the image data information Img0. Then the mould is optimized with the imaging result and data analysis result Img10. Repeating these steps, the mould is optimized gradually at the same time as obtaining the imaging result and data analysis result with the higher quality. When the information of the mould is accurate enough, the imaging result and data analysis result with the higher quality may also be obtained without calibrating, correcting and optimizing the imaging system. The present embodiment may achieve the advantages of saving time and cost as the embodiment 1 when the information of the mould is accurate enough in the future.

Embodiment 3

As shown in FIGS. 13, 14, 17, 18, an individualized imaging method of the disclosure includes the following steps:
S1, imaging, by an imaging system A, a mould of an object to be imaged, to obtain image data information Img0;
S2, calibrating, correcting and optimizing an imaging system B with the image data information Img0, scanning and imaging, by the calibrated, corrected and optimized imaging system B, the object to be imaged, to obtain image data information Img1; and
S3, processing the image data information Img0 and the image data information Img1 to obtain an A-B fused imaging result and data analysis result Img10.

Figure 12:
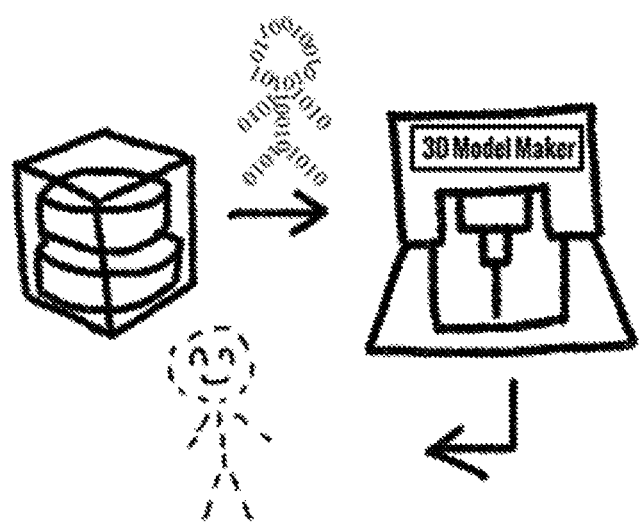
FIG. 12 is a flow chat illustrating manufacturing a mould by using a 3D module manufacturing device in an individualized imaging method of the disclosure.
Figure 13:
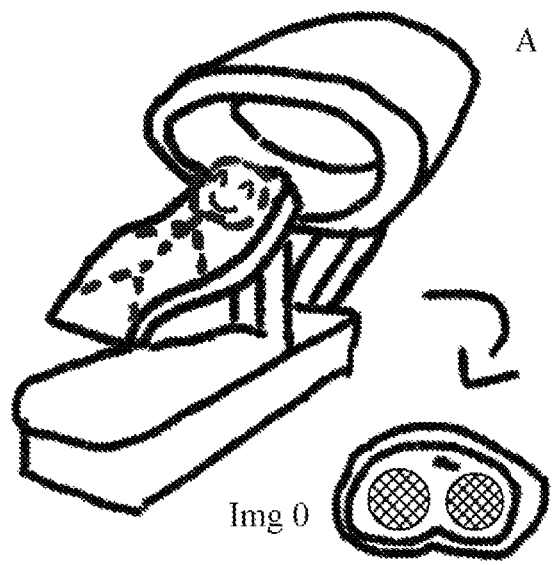
FIG. 13 is a schematic diagram illustrating imaging the mould manufactured in FIG. 12 by using an imaging system A in an individualized imaging method of the disclosure.
Figure 14:
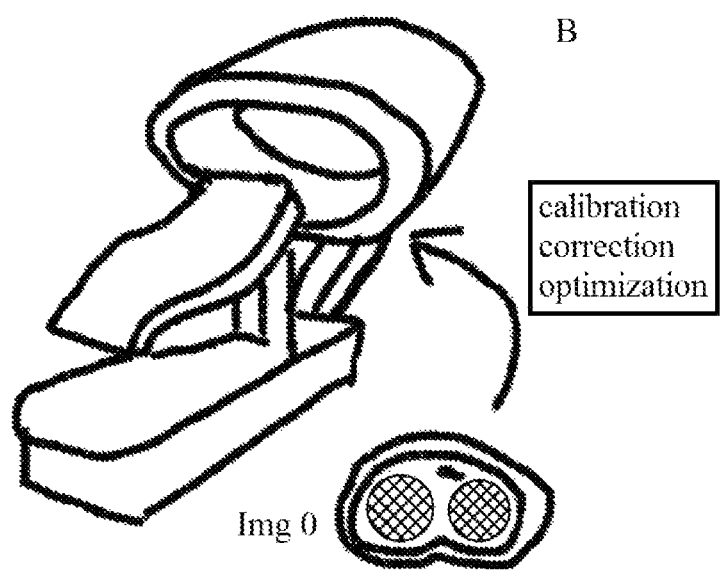
FIG. 14 is a schematic diagram illustrating calibrating, correcting and optimizing an imaging system B with image data information of the mould obtained in FIG. 13 in an individualized imaging method of the disclosure.
Figure 15:
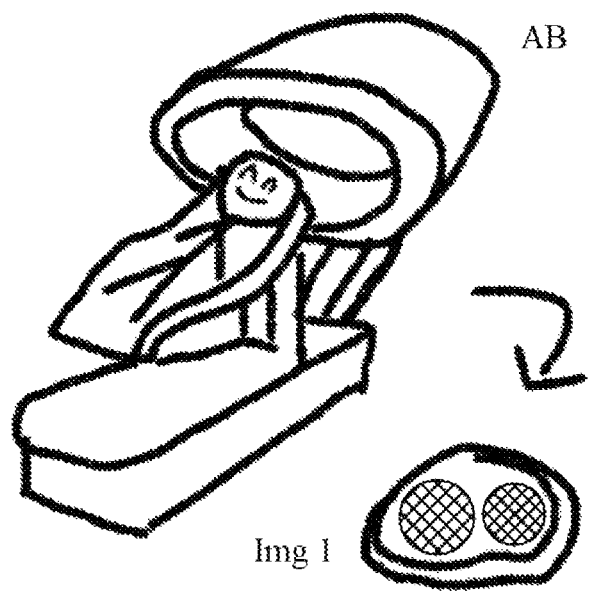
FIG. 15 is a schematic diagram illustrating imaging a body by using a combined imaging system AB in which the imaging system B of the combined imaging system is the calibrated, corrected and optimized imaging system in FIG. 14 in an individualized imaging method of the disclosure.

As shown in FIG. 12, a mould is made by hand or by a 3D module manufacturing device and method, such as 3D printing or injection molding or die casting and so on, before the step S1 of the embodiment.

The embodiment is mainly for obtaining combined imaging data. In a specific embodiment, for example, the image data information Img0 is obtained by performing CT imaging on the object to be imaged. The PET is calibrated, corrected and optimized with the image data information Img0. Then the image data information Img1 is obtained by scanning and imaging the object to be imaged with the PET. Subsequently, the image data information Img0 and the image data information Img1 are processed. Thus, a PET-CT fused imaging result and data analysis result Img10 is obtained.

In another specific embodiment, for example, the image data information Img0 is obtained by performing CT imaging on the object to be imaged. The SPECT is calibrated, corrected and optimized with the image data information Img0. Then the image data information Img1 is obtained by scanning and imaging the object to be imaged with the SPECT. Subsequently, the image data information Img0 and the image data information Img1 are processed. Thus, a SPECT-CT fused imaging result and data analysis result Img10 is obtained.

In the embodiment, the object to be imaged is not imaged by the imaging system A in obtaining the fused imaging result and data analysis result Img10. It may avoid that the object to be imaged bears unnecessary physical injury and avoid spending too much time. For example, the harm of the radiation dose in the CT imaging in the above specific embodiment is relatively large to human body. It may prevent the human body from the CT radiation by only using the imaging information of the mould to obtain the fused imaging result and data analysis result Img10.

In the embodiment, the individualized imaging method further includes step S4: optimizing the mould with the fused A-B imaging result and data analysis result Img10. By repeating S1-S4, the mould is optimized gradually at the same time as obtaining the imaging result and data analysis result with the higher quality. The embodiment may also achieve the advantages of saving time and cost as the embodiment 1 when the information of the mould is accurate enough in the future.

Figure 19:
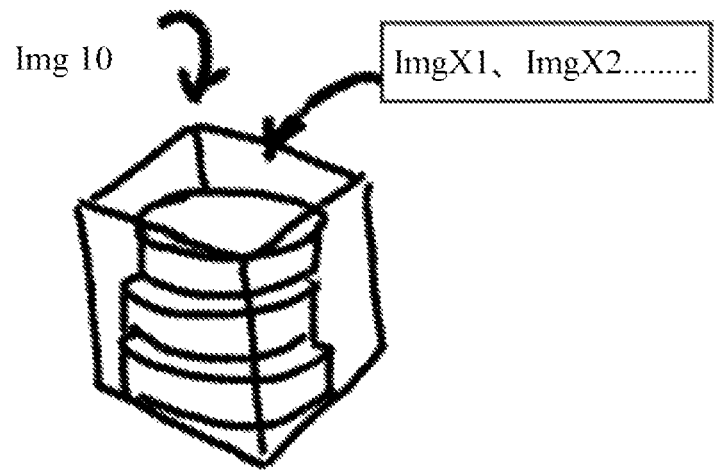
FIG. 19 illustrating a concept of obtaining a plurality of human images by combined imaging in which the plurality of human images may be classified in an individualized imaging method of the disclosure.

As shown in FIG. 19, FIG. 19 indicates a material library. The material library includes imaging results and data analysis results Img10 of objects to be imaged. A database is established for the Img10. According to one of the mould manufacturing methods, for every single object to be imaged, the imaging results and data analysis results in the past are processed to make the mould. According to another method, image results and data analysis results Img10 of several people are classified into ImgX1, ImgX2 Thus, the objects to be imaged are classified. For each class, processing, such as averaging, the database generated by imaging the objects to be imaged through various imaging systems is performed, and then the mould is made with the obtained information.

Embodiment 4

As shown in FIGS. 13, 14, 15, and 18, an individualized imaging method of the disclosure includes the following steps:

S1, imaging, by an imaging system A of an A-B combined imaging system, a mould of an object to be imaged, to obtain image data information Img0;

S2, calibrating, correcting and optimizing an imaging system B of the A-B combined imaging system with the image data information Img0, performing, by the A-B combined imaging system with the calibrated, corrected and optimized imaging system B, combined imaging on the object to be imaged, to obtain image data information Img1; and S3, processing the image data information Img0 and the image data information Img1 to obtain an A-B fused imaging result and data analysis result Img10.

The difference between the present embodiment and the embodiment 3 is the imaging system itself in the present embodiment is a combined imaging system. The object to be imaged needs A and B imaging simultaneously in the combined imaging.

The individualized imaging method further includes step S4: optimizing the mould with the fused A-B imaging result and data analysis result Img10. According to the method of the embodiment, the imaging of the mould is more and more close to the imaging of the object to be imaged. The image data information with a higher quality may be obtained by using the image data information achieved by imaging the more optimized mould to optimize the image data information achieved by imaging the object to be imaged. So, when the priori knowledge of the mould is accurate enough, on some occasions, some imaging systems with low degree of injury to human body may be selected to image the object to be imaged. Such as for PEC-CT or SPECT-CT combined imaging, low dose of CT radiation may be used for the CT imaging.

The present embodiment may also achieve the advantages of saving time and cost as the embodiment 1 when the information of the mould is accurate enough in the future.

Embodiment 5

Figure 16:
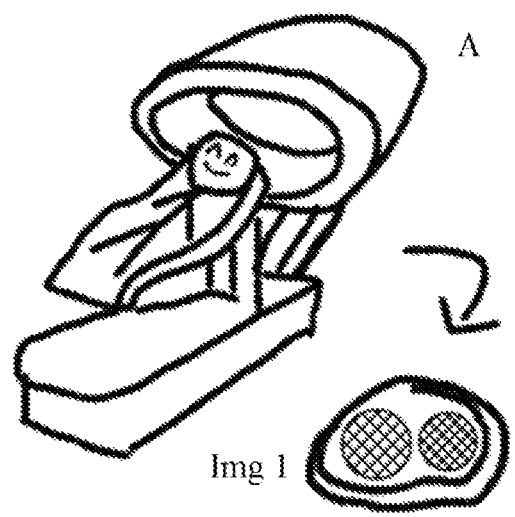
FIG. 16 is a schematic diagram illustrating imaging a body by using the imaging system A in an individualized imaging method of the disclosure.
Figure 17:
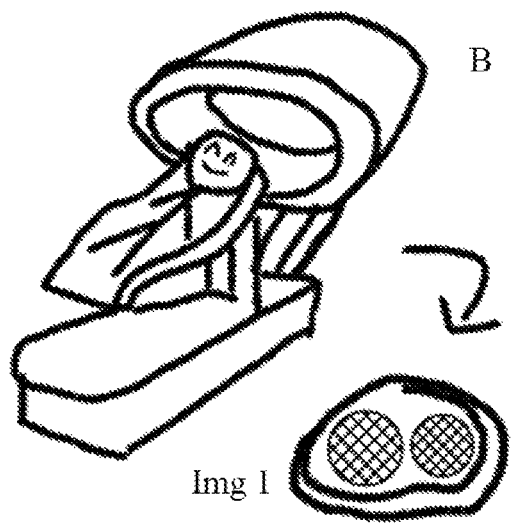
FIG. 17 is a schematic diagram illustrating imaging a body by using the imaging system B in which the imaging system B is the calibrated, corrected and optimized imaging system in FIG. 14 in an individualized imaging method of the disclosure.
Figure 18:
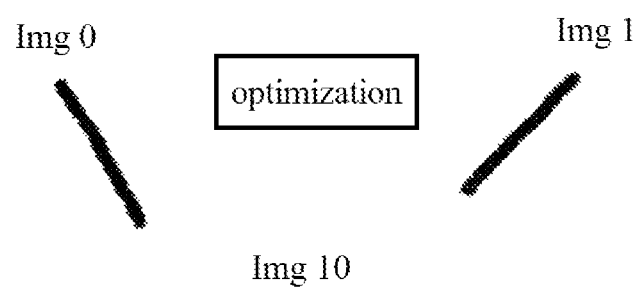
FIG. 18 illustrating obtaining imaging result and data analysis result of new combined imaging by optimizing the image data information of the mould obtained in FIG. 13 and the image data information of the body obtained in FIG. 15 in an individualized imaging method of the disclosure.

As shown in FIG. 16, an individualized imaging method of the disclosure includes the following steps:

S1, imaging, by an imaging system A of an A-B combined imaging system, a mould of an object to be imaged, to obtain image data information Img0;

S2, imaging, by the imaging system A of the A-B combined imaging system, the object to be imaged, to obtain image data information Img1;

S3, processing the image data information Img0 and the image data information Img1 to obtain an integrated image data information Img2 and calibrating, correcting and optimizing an imaging system B of the A-B imaging system with the image data information Img2;

S4, imaging, by the calibrated, corrected and optimized imaging system B, the object to be imaged to obtain image data information Img3; or performing, by the A-B combined imaging system with the calibrated, corrected and optimized imaging system B, combined imaging on the object to be imaged to obtain image data information Img3; and S5, processing the image data information Img1 and Img3 or processing the image data information Img0 and Img3 or processing the image data information Img0, Img1 and Img3 or processing the image data information Img2 and Img3, to obtain an A-B fused imaging result and data analysis result Img10.

The difference between the present embodiment and the embodiment 4 is that, when calibrating, correcting and optimizing the imaging system B in the embodiment, it needs not only the image data information Img0 obtained by imaging the mould via the imaging system A of the A-B combined imaging system but also the image data information Img1 obtained by imaging the object to be imaged via the imaging system A of the A-B combined imaging system. The imaging system B of the A-B combined imaging system is calibrated, corrected and optimized with the image data information Img0 and the image data information Img1.

The difference between the present embodiment and the embodiment 4 further is that, after calibrating, correcting and optimizing the B imaging system, it may select to perform A-B combined imaging on the object to be imaged or may not image the object to be image via the imaging system A and only image the object to be image via the imaging system B. This is mainly suitable for some occasions in which the imaging system A is harmful to human body. For example, in PET-CT imaging, the CT radiation dose of the imaging system A is harmful to human body. So when the data quality meets the requirements, it may choose not to repeat the CT imaging to prevent human body from injury again.

The object to be imaged in the embodiment is imaged twice at the same time. Because the mould is imaged first, it may not only have the optimized function to the subsequent imaging data but also help to select imaging system A, which has less harm to the object to be imaged and lower cost, for next imaging via the imaging system A. Such as, for PET/CT combined imaging, after CT imaging is performed on the mould, if PEC/CT imaging is performed on the object to be imaged, the CT in the PEC/CT combined imaging may be low cost CT so to reach the object of saving cost. The CT in the PEC/CT combined imaging may also have low radiation dose so the radiation dose born by the object to be imaged may be greatly reduced.

In the embodiment, the individualized imaging method further includes step S6: optimizing the mould with the fused A-B imaging result and data analysis result Img0. According to the method of the embodiment, the imaging of the mould is more and more close to the imaging of the object to be imaged. The image data information with a higher quality may be obtained by using the image data information achieved by imaging the more optimized mould to optimize the image data information achieved by imaging the object to be imaged. So, when the priori knowledge of the mould is accurate enough, on some occasions, some imaging systems with low degree of injury to human body may be selected to image the object to be imaged. Such as for PEC-CT or SPECT-CT combined imaging, low dose of CT radiation may be used for the CT imaging.

The present embodiment may also achieve the advantages of saving time and cost as the embodiment 1 when the information of the mould is accurate enough in the future.

Hereinafter an individualized imaging method of the disclosure is further described by a specific imaging system of an embodiment.

Embodiment 6

As shown in FIG. 21 to FIG. 24, an individualized imaging method of the disclosure includes the following steps:
S1, imaging a mould of an object to be imaged via a CT, to obtain image data information Img0;
S2, calibrating, correcting and optimizing a PET based on the image data information Img0,
S3, performing combined imaging on the object to be image via a PET/CT to obtain image data information Img1, or performing PET and CT imaging respectively and then performing image fusing to obtain image data information Img1, or performing imaging only via the PET to obtain image data information Img1.
S4, optimizing the image data information Img0 and the image data information Img1 to obtain PET/CT fused imaging result and data analysis result Img10.

Alternatively, S4 may also be as follows: when performing PET/CT combined imaging on the object to be imaged or performing PET and CT imaging respectively and then performing fusing, the combined imaging result or the fused imaging result may be directly taken as the imaging result and data analysis result Img10. Because there is no need to use the priori image data information Img0 to optimize the subsequent imaging, although the quality of the optimized imaging result and data analysis result is higher.

Figure 20:
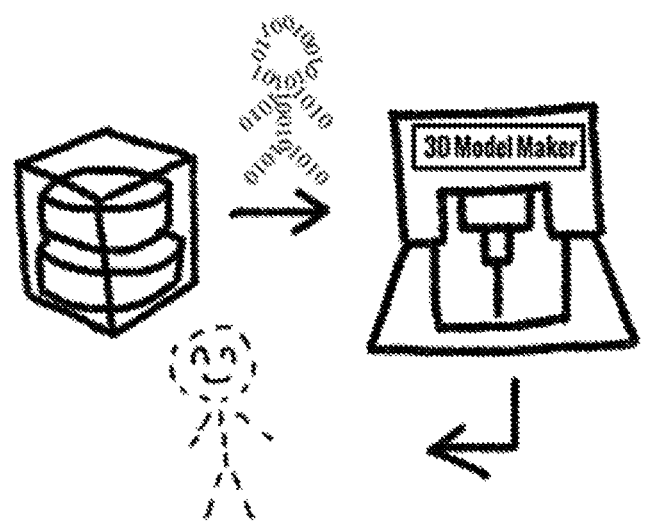
FIG. 20 is a flow chat illustrating manufacturing a mould by a 3D module manufacturing device in an individualized imaging method of the disclosure.
Figure 21:
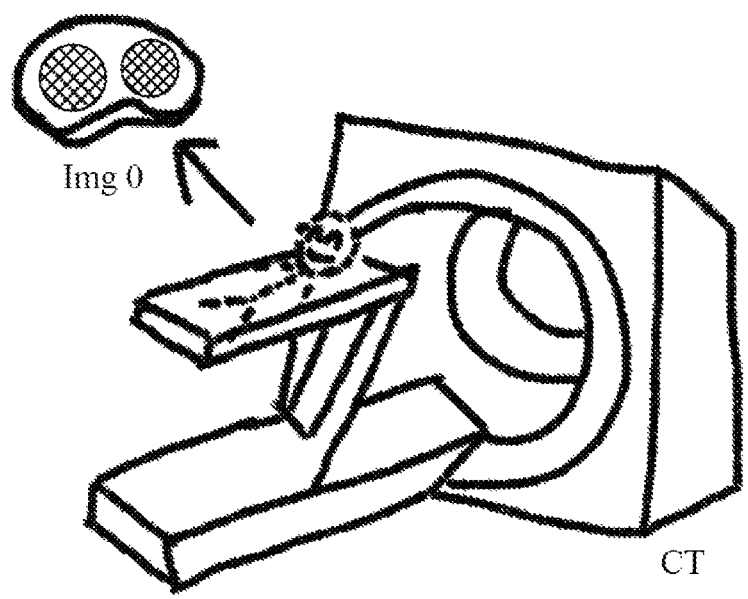
FIG. 21 is a schematic diagram illustrating imaging the mould manufactured in FIG. 20 by using an CT imaging system in an individualized imaging method of the disclosure.
Figure 22:
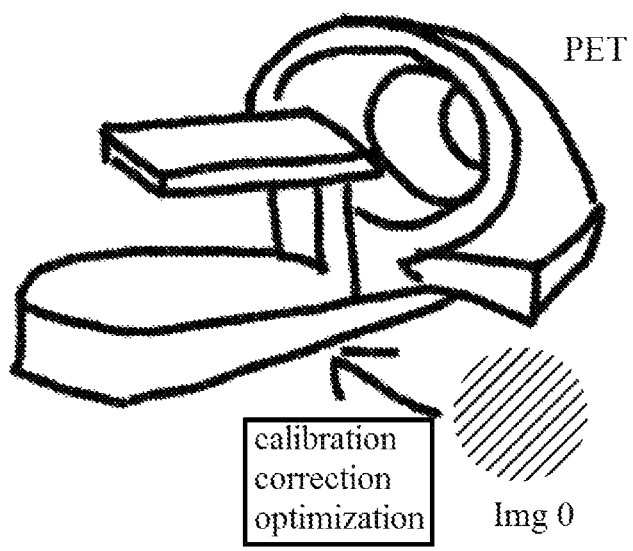
FIG. 22 is a schematic diagram illustrating calibrating, correcting and optimizing an PET imaging system with image data information of the mould obtained in FIG. 21 in an individualized imaging method of the disclosure.
Figure 23:
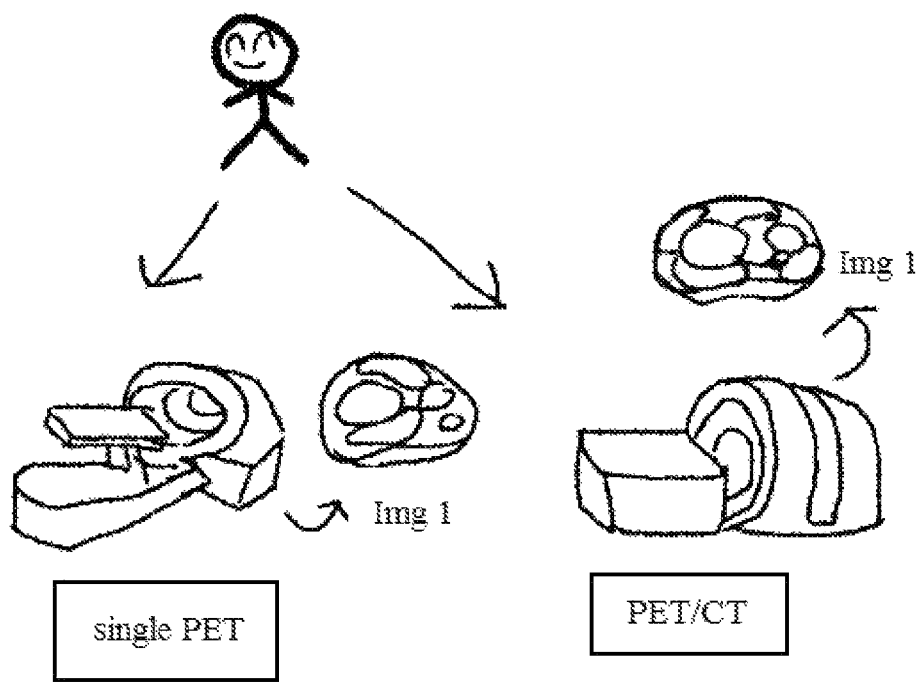
FIG. 23 is a schematic diagram illustrating imaging a body by using the single PET or the PET/CT combined imaging method in which the PET imaging system is the calibrated, corrected and optimized PET imaging system in FIG. 22 in an individualized imaging method of the disclosure.
Figure 24:
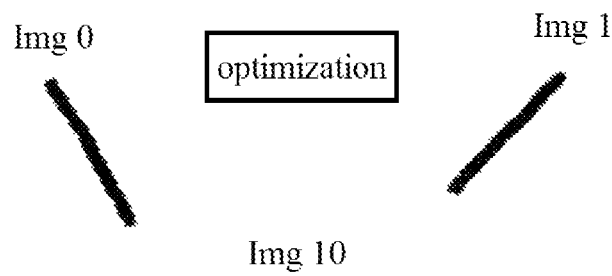
FIG. 24 is a schematic diagram illustrating obtaining imaging result and data analysis result of new combined imaging by optimizing the image data information of the mould obtained in FIG. 21 and the image data information of the body obtained in FIG. 23 in an individualized imaging method of the disclosure.

As shown in FIG. 20, a mould is made by hand or by a 3D module manufacturing device and method, such as 3D printing or injection molding or die casting and so on before the step S1 of the embodiment.

Figure 25:
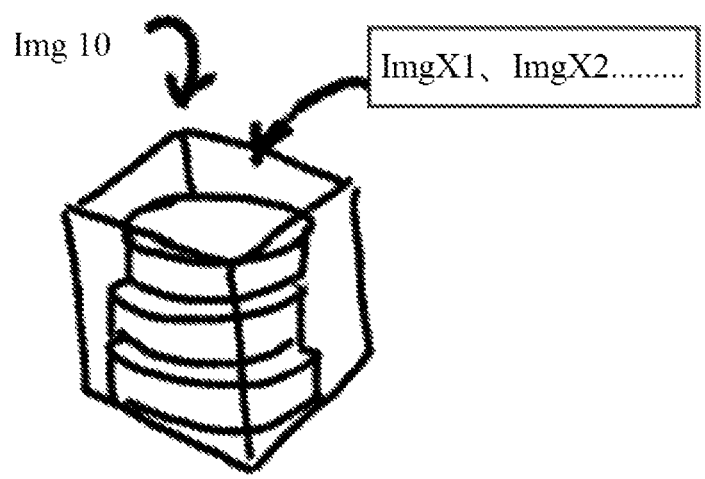
FIG. 25 illustrating a concept of obtaining a plurality of human images by combined imaging in which the plurality of human images may be classified in an individualized imaging method of the disclosure.

As shown in FIG. 25, FIG. 25 indicates a material library. The material library includes imaging results and data analysis results Img10 of objects to be imaged. A database is established for the Img10. According to one of the mould manufacturing methods, for every single object to be imaged, the imaging results and data analysis results in the past are processed to make the mould. According to another method, image results and data analysis results Img10 of several people are classified into ImgX1, ImgX2 Thus, the objects to be imaged are classified. For each class, the database generated by imaging the objects to be imaged through various imaging systems is averaged, and then the mould is made with the obtain information.

The calibration in step S2 may adopt a normalization method. The correction may adopt a scattering correction.

In the step S2, the image data information Img1 may be obtained by performing PET/CT combined imaging on the object to be imaged, and the PET is calibrated, corrected and optimized with the CT image of the mould. In such a case, PET and low cost CT may be adopted. The low cost CT works in a relatively high radiation dose to image the mould of the object to be imaged. The imaging result is used to calibrate, correct, optimize the PET imaging system, and the CT system is also optimized at the same time. Then combined imaging, i.e. the PET imaging in combination with the CT imaging which works in a low radiation dose, is performed on the object to be imaged.

In the step S2, the image data information Img1 may be obtained only by performing PET imaging, and the PET is calibrated, corrected and optimized with the CT image of the mould. In such a case, the object to be imaged (patients or animals) may not accept the radiation (this occupies the most radiation dose in the PET/CT) brought by the CT imaging. The radiation dose is greatly reduced and the quality of the PET imaging is maintained.

In the step S2, the PET imaging and the CT imaging may be performed respectively, and before performing PET imaging, the PET may be calibrated, corrected and optimized with the CT image of the mould or the PET may be calibrated, corrected and optimized with the CT image of the mould in combination with the CT image of the object to be imaged. The present solution combines the CT imaging of the object to be imaged with the CT imaging of the 3D mould of the object to be imaged to generate an anatomical imaging result of the object to be imaged. The PET system is further calibrated, corrected and optimized based on the result. Image fusing may be performed on the functional imaging obtained by the PET imaging system and the anatomical imaging obtained by the CT imaging system to obtain a fused functional and anatomical image. In this case it includes a first implementation solution. That is, A relatively low CT radiation dose may be selected for the object to be imaged to obtain a PET/CT image with a high quality. In this case it further includes a second implementation solution. That is, PET and low cost CT are adopted for the object to be imaged. The low cost CT works in a relatively high radiation dose to image the mould of the object to be imaged. The imaging result is used to calibrate, correct, optimize the PET imaging system and optimize the CT system at the same time. Then the PET imaging and the CT imaging which works in a low radiation dose are performed on the object to be imaged respectively. The difference between the first implementation solution and the second implementation is that the dose of the CT chosen in the first implementation solution is relatively low. But the CT itself in the first implementation solution may not be low cost and may be high cost. However the CT in the second implementation solution is low cost.

Generally speaking, it includes three situations for the choice of the CT imaging of the PET/CT combined imaging. For the first situation, patients and animals may choose not to accept the radiation brought by the CT imaging (this occupies the most radiation dose in the PET/CT). The radiation dose is greatly reduced and the quality of the PET imaging is maintained. For the second situation, the CT imaging of the object to be imaged with the CT imaging of the 3D mould of the object to be imaged is combined to generate the anatomical imaging result of the object to be imaged and the PET imaging system is further calibrated, corrected and optimized based on the result. Image fusing may be performed on the functional imaging obtained by the PET imaging system and the anatomical imaging obtained by the CT imaging system to obtain the fused functional and anatomical image. In this case a relatively low CT radiation dose may be selected for the object to be imaged to obtain a high quality PET/CT image. For the third situation, PET and low cost CT are adopted. The low cost CT works in a relatively high radiation dose to image the mould of the object to be imaged. The imaging result is used to calibrate, correct, optimize the PET imaging system and optimize the CT system at the same time. Then the PET imaging and the CT imaging which works in a low radiation dose are performed on the object to be imaged. In the above three situations, in order to obtain the same PET imaging qualities, the PET imaging systems may all be established with lower cost or the patients accept a lower PET tracer radiation dose. Conversely, the quality of the PET imaging may be higher by adopting the PET imaging system with the same cost and accepting the same PET tracer radiation dose.

Each of the imaging systems of the embodiments of the disclosure may be CT, MRI, SPECT, PET, DR, or CR.

In all the embodiments of the disclosure, for CT, it may coordinate with an image reconstruction method requiring a small amount of data to perform reconstruction with a small amount of dose. It may fuse other density data to perform multi-parameter estimation. For MRI, it may coordinate with magnetic resonance with low quality or low field to develop super-resolution imaging.

The imaging system is calibrated, corrected and optimized with the image data information Img0 of the mould in all the embodiments of the disclosure because the imaging systems of the conventional medical institutions are all common for most people. The imaging system is adjusted by the imaging of the mould, so that the imaging system is adjusted into a state suitable for the object to be imaged. So, a best imaging effect may be obtained. That is to say, for the imaging systems with an ordinary performance level, although the costs of the imaging systems themselves are not saved, the imaging qualities may be improved. Of course, for some imaging systems with a non-ordinary performance level, when ensuring the imaging qualities, considering from the point of saving costs of the imaging systems, it may choose imaging systems with relatively low performance parameters. The spare parts of these imaging systems with low performance parameters themselves have low costs, so the entire manufacturing costs of the imaging systems are relatively low.

The individualized imaging methods of the embodiments of the disclosure fully utilize the priori knowledge of human. A mould is established for an individual. The mould is used to calibrate, correct the CT imaging or PET imaging or MRI imaging or multiple combined imaging to obtain an imaging result and data analysis result with a higher quality.

For the later imaging development, by the enlightenment of the disclosure, as long as a tailored mould is made for every object to be imaged, the unnecessary imaging may be avoided. The imaging system may be calibrated, corrected and optimized by the information of the mould at the same time.

The priori knowledge of human body used in the embodiments of the disclosure is as follows: the priori knowledge of human body obtained by performing imaging on individual is used to make the mould for the individual or the priori knowledge of objects to be imaged is used to make mould after being classified and averaged, then the mould is used to optimize the imaging system and the imaging data information, as pointed in the above embodiment.

Of course, the priori knowledge of human body may also be useful for the subsequent human body scanning Such as, pre-scanning chest and abdomen may cumulatively obtain the influence of respiratory movement on the shape and the location of the chest and abdomen organs. Thus, for subsequent scanning, we may just need a short time scanning to utilize the information of the preceding scanning to accurately obtain the shape and the location of the chest and abdomen organs. Or we may utilize the scanning result of the PET to pre-determine the location of the focus and then utilize the CT to scan to reduce the dose of the CT and so on.

In the multiple embodiments of the disclosure, the imaging system is calibrated, corrected and optimized with the image data information Img0 of the mould. If the imaging system of the mould and the calibrated, corrected and optimized imaging system are the same one, calibration, correction and optimization express the meaning of optimization. If the imaging system of the mould and the calibrated, corrected and optimized imaging system are different imaging systems, there exists the process of calibration, correction and optimization. The methods of calibration, correction and optimization are different for different imaging systems. Hereinafter, PET-CT is taken as an example.

The CT is used to perform attenuation correction on the PET such that the PET obtains more accurate imaging.

The data obtained by the PET contains an attenuation effect. Because the attenuation effect may occur when 511 keV gamma penetrating human body. If the corresponding correction is not done, the image will have contrast error, quantitative error and focus is unrecognizable. Since CT imaging may also obtain the distributions of attenuation coefficients of different tissues and organs of human body, the signal noise ratio of CT image is higher and the imaging speed is fast, the PET generally adopts the CT imaging for the attenuation correction to the PET data.

The method is as follows: CT collecting data; reconstructing the CT image; obtaining the CT image; converting the CT image to obtain a 511 keV attenuation image (the energy range of the CT is 40-140 keV and the PET is 511 keV; the attenuation values are not the same; conversion is necessary; the method includes segmentation method, mapping method, dual-energy CT method and so on); obtaining the PET data by PET scanning; utilizing the attenuation image of the CT conversion to perform attenuation correction; utilizing the corrected PET data to perform image reconstruction; obtaining the PET image.

The PET is scattering corrected by the CT so that the PET may achieve more accurate imaging.

The data of PET scanning includes not only the true event, but also the scattering event and the random event. The scattering event causes the wrong location of the photon, the wrong estimation of contrast and quantization of the image, and has an effect on the recognition of the focus. The PET data is scattering corrected generally with the CT image. The process is as follows:

1, performing image reconstruction on the PET attenuation (A data) which is not scattering corrected, to obtain an initial image;
2, simulating the process of PET scanning with the PET active image, the CT attenuation image, to obtain an estimated distribution of scatter and true event;
3, performing scattering correction on the PET data which is not scattering corrected in 1 with the distribution of the scatter and true event in 2, to obtain corrected PET data (B data);
4, performing PET image reconstruction on the data (B data) outputted in 3, to obtain an optimized PET image.

The individualized imaging methods of the embodiments of the disclosure fully utilize the priori knowledge of human. A mould is established for an individual. The image data information of the mould may be utilized to optimize the imaging system and the image data information of the object to be imaged and the mould may be optimized further. By repeating this, the imaging result and data analysis result with the higher quality may be obtained.

Comparing with the conventional technology, the advantages of the disclosure includes:
(1) the image data information of the object to be imaged is further optimized with the imaging result of the mould, further more the imaging result and data analysis result with the higher quality may be obtained;
(2) the imaging system is corrected and optimized with the imaging result of the mould to place the imaging system in the state most suitable for the object to be imaged, further more the imaging result and data analysis result with the higher quality may be obtained;
(3) the imaging result and data analysis result with the higher quality may be obtained by using the mould, then the mould is optimized with the imaging result and data analysis result with the higher quality; by repeating this, the image data information obtained after imaging the mould is more accurate;
(4) for imaging systems with greater radiation, the amount of radiation born by the object to be tested may be reduced by imaging the mould, rather than imaging the actual object to be tested.

From the above descriptions of the embodiments, it can be clearly understood by those skilled in the art that all or some of the steps in the above embodiments may be performed by software and necessary general hardware platform. In this understanding, the technical solutions in essence or part of the contribution to the conventional technology of the disclosure may be performed by a software product. The computer software product may be stored in storage medium, such as ROM/RAM, a magnetic disk or an optical disk and include several instructions to make a computer device (which may be a personal computer, a server or a multimedia gateway or the like communication device) perform all the embodiments or a part of methods according to the embodiments of the disclosure.

It should be noted that the various embodiments in the application are described progressively. The same or similar parts of the various embodiments can be referred to mutually. Each embodiment focuses on the difference from other embodiments. Especially, for the embodiments of the apparatus and systems, since they are similar to the embodiments of the methods, are relatively described simply. Part of the method description can be referred to explain the corresponding parts. The embodiments of the apparatus and systems described above are merely schematic. The units as discrete components may be or not be physically discrete. The displayed components as units may be or not be physical units. That is to say they may be at one place or distributed to multiple network units. All or part of the modules may be selected to perform the objects of the solutions of the embodiments based on the actual demand. Those skilled in the art may understand and implement without inventive labor.

The above descriptions are the better embodiments of the disclosure, not intended to limit the protective field of the disclosure. All the amendments, equivalent substitutions, improvements under the spirit and principle of the disclosure are all in the protective field of the disclosure.

The invention claimed is:

1. An individualized imaging method, comprising:
obtaining first image data information of a mould of an object to be imaged;
calibrating, correcting and optimizing an imaging system with the first image data information, scanning and imaging the object to be imaged to obtain second image data information by the calibrated, corrected and optimized imaging system; and
optimizing the first image data information and the second image data information to obtain an imaging result and data analysis result with a higher quality,
wherein the mould of the object to be imaged is made according to density information or function information obtained by an imaging system imaging the object to be imaged, the density information is structure information that a material with the same density as human tissues is utilized to simulate different organs or tissues, the function information is simulated by reserving corresponding space in the mould to add drug taking part in relative function activities.

2. The individualized imaging method according to claim 1, further:
optimizing the mould with the imaging result and data analysis result with the higher quality.

3. The individualized imaging method according to claim 1, wherein the first image data information is obtained by obtaining data of the mould and extracting parameters from the data, or the first image data information is obtained directly from imaging operation of the imaging system.

4. An individualized imaging method, comprising:
imaging a mould of an object to be imaged to obtain first image data information by a first imaging system;
calibrating, correcting and optimizing a second imaging system with the first image data information, scanning and imaging the object to be imaged to obtain second image data information by the calibrated, corrected and optimized second imaging system; and
processing the first image data information and the second image data information to obtain a fused imaging result and data analysis result;
wherein the mould of the object to be imaged is made according to density information or function information obtained by an imaging system imaging the object to be imaged; the density information is structure information that a material with the same density as human tissues is utilized to simulate different organs or tissues; the function information is simulated by reserving corresponding space in the mould to add drug taking part in relative function activities.

5. The individualized imaging method according to claim 4 further comprising:
optimizing the mould with the fused imaging result and data analysis result.

* * * * *